(12) United States Patent
Matsumoto et al.

(10) Patent No.: US 11,299,699 B2
(45) Date of Patent: Apr. 12, 2022

(54) CULTURE CONTAINER

(71) Applicant: NIHON UNIVERSITY, Tokyo (JP)

(72) Inventors: Taro Matsumoto, Tokyo (JP);
Tomohiko Kazama, Tokyo (JP);
Kazuhiro Hagikura, Tokyo (JP)

(73) Assignee: NIHON UNIVERSITY, Tokyo (JP)

( * ) Notice: Subject to any disclaimer, the term of this patent is extended or adjusted under 35 U.S.C. 154(b) by 304 days.

(21) Appl. No.: 15/771,839

(22) PCT Filed: Nov. 1, 2016

(86) PCT No.: PCT/JP2016/082413
§ 371 (c)(1),
(2) Date: Apr. 27, 2018

(87) PCT Pub. No.: WO2017/078007
PCT Pub. Date: May 11, 2017

(65) Prior Publication Data
US 2018/0320123 A1 Nov. 8, 2018

(30) Foreign Application Priority Data
Nov. 6, 2015 (JP) .............................. JP2015-218569

(51) Int. Cl.
*C12M 1/12* (2006.01)
*C12M 1/00* (2006.01)

(52) U.S. Cl.
CPC ............ *C12M 23/34* (2013.01); *C12M 23/04* (2013.01)

(58) Field of Classification Search
CPC .............................. C12M 23/04; C12M 23/34
See application file for complete search history.

(56) References Cited

U.S. PATENT DOCUMENTS 4,121,976 A * 10/1978 Gleeson ................. C12M 23/08
215/6
4,640,895 A * 2/1987 Davis ..................... C12M 23/08
215/6

(Continued)

FOREIGN PATENT DOCUMENTS

CN 202849407 4/2013
JP 62-296873 12/1987

(Continued)

OTHER PUBLICATIONS

Aso et al., "Isolation, primary culture, and clinical application of human adipocytes", Organ Biology, 2014, pp. 60-65, vol. 21, No. 1.

(Continued)

*Primary Examiner* — Lydia Edwards
(74) *Attorney, Agent, or Firm* — Greenblum & Bernstein, P.L.C.

(57) ABSTRACT

A culture container includes: a culture container body; a partition plate disposed in the vicinity of a bottom of the culture container body to face the bottom so that a culture region is formed as a culture region between the partition plate and the bottom; and a sample inlet/outlet provided in the culture container body, the culture region and the sample inlet/outlet communicating with each other via an opening formed adjacent to one end of the partition plate. With the culture container and a culture method using this container, a large amount of adipocytes can be cultured at one time with easy handling. Dedifferentiation of a large amount of adipocytes and removal of cells having failed to dedifferentiate can be efficiently accomplished.

12 Claims, 11 Drawing Sheets

| 1 | CULTURE CONTAINER | 15 | PARTITION PLATE |
| 11 | CULTURE CONTAINER BODY | 15a | EDGE PLATE |
| 11a | SUPPORTING PORTION | 19 | SAMPLE INLET/OUTLET |
| 11b | OPENING | A1 | CULTURE REGION |
| 11c | BOTTOM | A2 | NON-CULTURE REGION |
| 13 | COVER | C | ADIPOCYTES |

(56) References Cited

U.S. PATENT DOCUMENTS

| | | | |
|---|---|---|---|
| 5,714,384 A * | 2/1998 | Wilson | C12M 23/24 435/297.1 |
| 2008/0044899 A1 | 2/2008 | Kano | |
| 2010/0129900 A1 | 5/2010 | Clark et al. | |
| 2011/0020923 A1 | 1/2011 | Lacey et al. | |
| 2014/0120607 A1 | 5/2014 | Abraham | |

FOREIGN PATENT DOCUMENTS

| | | |
|---|---|---|
| JP | 6-70756 | 3/1994 |
| JP | 7-079770 | 3/1995 |
| JP | 2011-024577 | 2/2011 |
| JP | 5055613 | 8/2012 |
| WO | 2004/111211 | 12/2004 |
| WO | 2010008566 | 1/2010 |
| WO | 2014066483 | 5/2014 |
| WO | 2014/142161 | 9/2014 |

OTHER PUBLICATIONS

Zhang et al., "Ceiling culture of mature human adipocytes: use in studies of adipocyte functions", Journal of Endocrinology, 2000, pp. 119-128, vol. 164.

Official Communication issued in Patent Application No. PCT/JP2016/082413, dated Jan. 24, 2017.

International Preliminary Report on Patentability for PCT/JP2016/082413, dated May 11, 2018, with English language translation.

Extended European Search Report for EP App No. 16862067.2 dated May 27, 2019.

Abraham et al. "Scale-up of Mammalian Cell Culture using a New Multilayered Flask", pp. 1-5, dated May 12, 2011, https://www.ncbi.nlm.nih.gov/pmc/articles/PMC3369669/pdf/jove-58-3418.pdf.

Shengjuan Wei et al. "Bovine dedifferentiated adipose tissue (DFAT) cells: DFAT cell isolation", Adipocyte, vol. 2, No. 3, dated Jul. 24, 2013.

Japanese Office Action, Japanese Patent Office, Application No. 2017-548768, dated May 21, 2020, English translation.

* cited by examiner

| 1 | CULTURE CONTAINER | 15 | PARTITION PLATE |
| 11 | CULTURE CONTAINER BODY | 15a | EDGE PLATE |
| 11a | SUPPORTING PORTION | 19 | SAMPLE INLET/OUTLET |
| 11b | OPENING | A1 | CULTURE REGION |
| 11c | BOTTOM | A2 | NON-CULTURE REGION |
| 13 | COVER | C | ADIPOCYTES |

18    ADHESIVE LAYER

A1　CULTURE REGION
A2　NON-CULTURE REGION

CULTURE CONTAINER

TECHNICAL FIELD

The present invention relates to a culture container by which cells can be easily cultivated with a small amount of medium. More particularly, the present invention relates to a culture container for use in ceiling culture of mature adipocytes and to a culture method using the culture container.

BACKGROUND ART

Urodeles such as newts are known as living creatures having high tissue regeneration potential. It has been revealed that the mechanism of the tissue regeneration involves dedifferentiation of terminally differentiated cells. When, for example, a limb of a newt is amputated, the muscle cells in the stump undergo dedifferentiation and change into cells called regeneration blastema which have multipotency and proliferative activity. It is becoming evident that the regeneration blastema proliferate and then differentiate into diverse kinds of tissue such as bones, blood vessels, and nerves, so that the limb is completely regenerated in several weeks. Such dedifferentiation of terminally differentiated cells has been generally considered not to occur in mammals.

Under such circumstances, Kano et al. have demonstrated that when mature adipocytes isolated from fat tissue of mammals including humans are cultured in-vitro by a method called ceiling culture, the resulting group of cells in a fibroblast-like form possesses high proliferative potential and multipotency (Patent Literature 1).

This indicates that even after terminal differentiation of cells, the terminally differentiated cells can be artificially dedifferentiated into undifferentiated cells by culture under appropriate conditions. The multipotent cells derived from mature adipocytes are also called dedifferentiated adipocytes (which may hereinafter be referred to as "DFAT cells").

DFAT cells have the following advantages over groups of cells such as cultured bone marrow mesenchymal stem cells and adipose-derived stem cells which are obtained by adhesion culture of stem cells present in trace amounts in adult tissue and the subsequent proliferation of the cultured cells: (1) DFAT cells can be obtained with a high purity without complicated screening operation because they are prepared from a mature adipocyte fraction; and (2) DFAT cells can be prepared from tissue of patients in poor general condition or elderly patients because the amount of the tissue required to be obtained is small (1 g or less). Additionally, although DFAT cells do not possess totipotency like that of iPS cells, DFAT cells can be quickly prepared in large amounts by a simple method without the use of genetic engineering or virus vectors, and are therefore expected soon to be clinically applied as donor cells for regenerative medicine. It is also considered that a banking system can be easily constructed by exploiting fat tissue discarded in surgical operations.

Furthermore, since DFAT cells can be prepared from a small amount of fat tissue regardless of age, they are expected as novel donor cells for regenerative medicine for patients who have thus far been believed to have difficulty undergoing autologous stem cell transplantation, such as patients with severe cardiac failure and elderly patients. As for clinical applications, DFAT cells are considered widely applicable to regeneration of various kinds of mesodermally-derived tissue such as bones, cartilages, blood vessels, cardiac muscles, and smooth muscles.

The outline of the conventional ceiling culture is illustrated in FIG. 11. The conventional ceiling culture includes the steps of: (a) obtaining fat tissue and performing collagenase treatment, filtration, and then low-speed centrifugation; (b) collecting suspended mature adipocyte fraction and culturing the mature adipocyte in a culture container filled with a medium (20% fetal bovine serum-supplemented DMEM); (c) replacing the medium and inverting the culture container upon confirmation that the mature adipocytes have adhered to the ceiling of the culture container and undergone cell division to produce DFAT cells presenting a fibroblast-like form and the DFAT cells have repeated cell division and proliferation to form a colony; and (d) subsequently performing normal adhesion culture.

CITATION LIST

Patent Literature

Patent Literature 1: Japanese Patent No. 5055613

SUMMARY OF INVENTION

Technical Problem

In the conventional ceiling culture method, for example, the step (b) mentioned above is carried out, as illustrated in FIG. 11, by a procedure consisting of: (i) adding about 41 ml of a medium (20% fetal bovine serum-supplemented DMEM) to a 12.5-cm$^2$ cell culture flask (culture container) 101 placed upright with its mouth facing upward, thereby filling the culture container body 111 up to the shoulder of the culture container body 111; (ii) adding a medium (about 40 µl) containing mature adipocytes (3 to 5×10$^5$ cells); (iii) further adding a medium (20% fetal bovine serum-supplemented DMEM) up to the rim of the sample inlet/outlet 119 of the culture container and capping the sample inlet/outlet 119 while deliberately avoiding entry of air; and (iv) culturing the mature adipocytes by allowing the culture container 101 to stand in a $CO_2$ incubator, with the bottom of the culture container 101 serving as a ceiling. However, this conventional procedure requires meticulous attention and technical proficiency.

There have therefore been demands for a method by which a large amount of cells can be cultured at one time with easy handling and for a culture container for use in such a method. Additionally, in order that dedifferentiated adipocytes (DFAT cells) prepared by ceiling culture may be practically used as therapeutic cells, a method enabling more efficient dedifferentiation of a large amount of adipocytes, a method enabling more efficient removal of cells having failed to dedifferentiate, and a culture container for use in such methods have also been demanded.

An object of the present invention is to provide a culture method and culture container by which a large amount of cells can be cultured at one time with easy handling.

Solution to Problem

The present invention relates to the following.

[1] A culture container including: a culture container body; a partition plate disposed in the vicinity of a bottom of the culture container body to face the bottom so that a culture region is formed between the partition plate and the bottom; and a sample inlet/outlet provided in a portion of the culture container body, the culture region and the sample inlet/outlet communicating with each other via an opening formed adjacent to one end of the partition plate.

[2] The culture container according to [1], wherein the partition plate includes an edge plate along an edge thereof adjacent to the opening, the edge plate projecting toward the bottom.

[3] The culture container according to [1] or [2], wherein the sample inlet/outlet is provided in a side surface or a ceiling of the culture container, being adjacent to the opening of the culture container.

[4] The culture container according to any one of [1] to [3], wherein the distance between the partition plate and the bottom is 3.5 mm to 5 mm.

[5] The culture container according to any one of [1] to [4], wherein the partition plate includes an adhesive layer on a major surface thereof facing the bottom.

[6] The culture container according to [5], wherein the adhesive layer is selected from the group consisting of laminin, fibronectin, type I collagen, and gelatin.

[7] The culture container according to any one of [1] to [6], wherein the partition plate has an air hole at a position adjacent to the other end remote from the opening.

[8] The culture container according to [7], wherein the partition plate includes an edge plate along an edge of the air hole, the edge plate projecting toward the bottom.

[9] The culture container according to any one of [3] to [8], wherein the opening and the air hole are opposed to each other substantially on the diagonal of the partition plate.

[10] The culture container according to any one of [1] to [9], wherein the culture container is a container for use in ceiling culture for dedifferentiation of adipocytes.

[11] A method of dedifferentiating adipocytes, including the steps of: charging a culture region of a culture container with mature adipocytes and a culture fluid, the culture container including a partition plate disposed in the vicinity of a bottom of the culture container to face the bottom so that the culture region is formed between the partition plate and the bottom, and a sample inlet/outlet communicating with the culture region via an opening of the culture region; adhering the mature adipocytes suspended in the culture fluid to the partition plate; and slightly tilting the culture container to discharge a portion of the culture fluid and mature adipocytes having failed to dedifferentiate from the culture region to the outside of the culture container through the opening and the sample inlet/outlet.

[12] The method of dedifferentiating adipocytes according to [11], wherein, in the adhering step, the mature adipocytes are adhered to the partition plate via an adhesive layer.

[13] The method of dedifferentiating adipocytes according to [11] or [12], wherein the angle of the tilting is 90 degrees or less.

[14] The method of dedifferentiating adipocytes according to [11], wherein the culture container is the culture container according to any one of [1] to [9].

Advantageous Effects of Invention

The present invention provides a culture method and culture container by which a large amount of cells can be cultured at one time with easy handling.

DESCRIPTION OF EMBODIMENTS

Figure 1A:
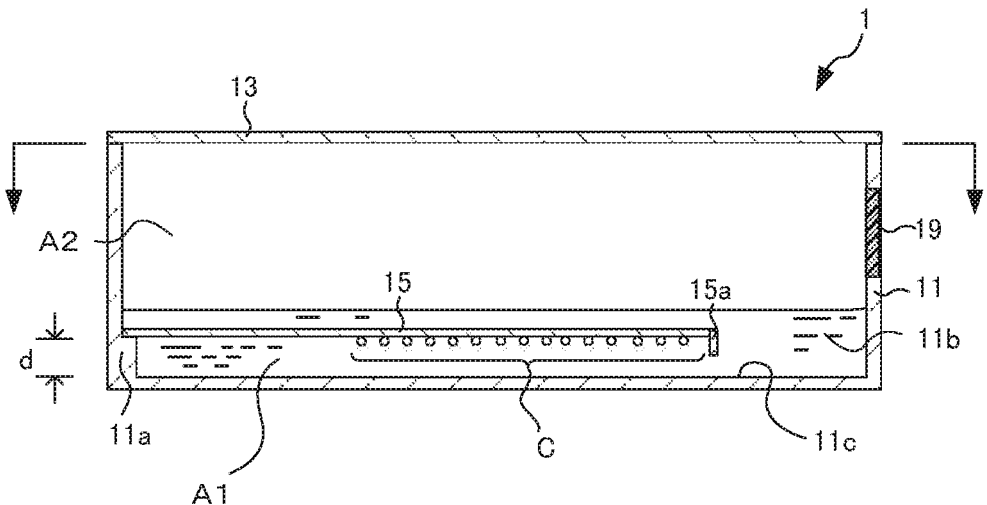
FIG. 1A is a side cross-sectional view illustrating a culture container according to the first embodiment which is in use.

Hereinafter, the present invention will be described with reference to embodiments. The present invention is not limited to the embodiments described below. Components having the same or similar functions are denoted by the same or similar reference signs in the drawings to avoid repeated description. It should be noted that the drawings are schematic. This means that the specific dimensions etc. of the components should be considered in light of the following description. It should be appreciated that the relationship or ratio between the dimensions of the components may vary among the drawings. Depending on the culture step, mature adipocytes and DFAT cells may coexist; however, only the term "mature adipocytes" is used in some parts of the specification and drawings for convenience of illustration.

(Culture Container According to First Embodiment)

Figure 1B:
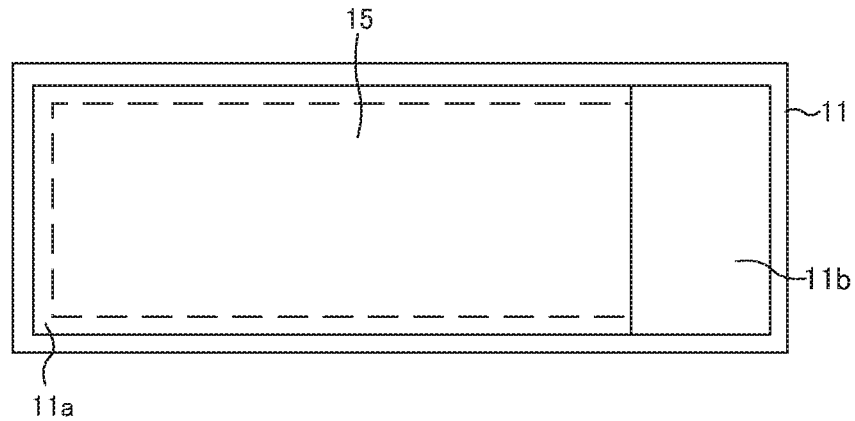
FIG. 1B is a top view illustrating the culture container without the ceiling.

FIG. 1A is a side cross-sectional view illustrating a culture container 1 according to the first embodiment which is in use. FIG. 1B is a top view illustrating the culture container 1 according to the first embodiment without the ceiling 13.

As illustrated in FIG. 1A, the culture container 1 includes: a culture container body 11; a partition plate 15 disposed in the vicinity of the bottom 11c of the culture container body 11 to face the bottom 11c so that a culture region A1 is formed between the partition plate 15 and the bottom 11c; a sample inlet/outlet 19 provided in a portion of the culture container body 11; and a ceiling (cover) 13 detachably attached to the culture container body 11. The culture region A1 and the sample inlet/outlet 19 communicate with each other via an opening formed adjacent to one end of the partition plate 15. In this embodiment, the opening is defined by the culture container body 11 and the one end of the partition plate 15. However, the present invention is not limited by such an opening. For example, the partition plate 15 may be disposed in the vicinity of the bottom 11*c* to extend over the entire bottom 11*c*, and may be provided with a communication hole that is located at a position adjacent to one end of the partition plate 15 and that extends from the ceiling-facing major surface of the partition plate 15 to the bottom-facing major surface of the partition plate 15.

According to the first embodiment, since the partition plate 15 is disposed in the vicinity of the bottom 11*c* of the culture container body 11 to face the bottom 11*c*, ceiling culture of mature adipocytes can be accomplished with a small amount of medium (culture fluid). This permits the culture container 1 to be slim and compact, thereby enabling observation of mature adipocytes C with an inverted phase contrast microscope.

Figure 3A:
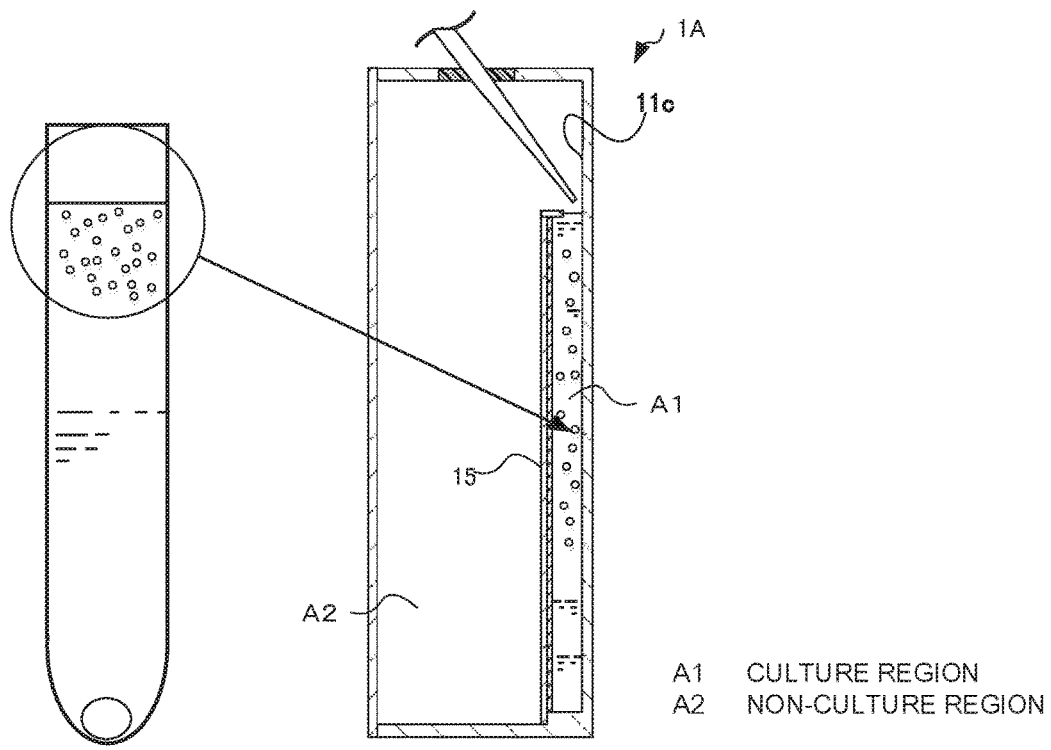
FIGS. 3A through 3G illustrates the steps of a culture method according to an embodiment of the present invention.
Figure 3B:
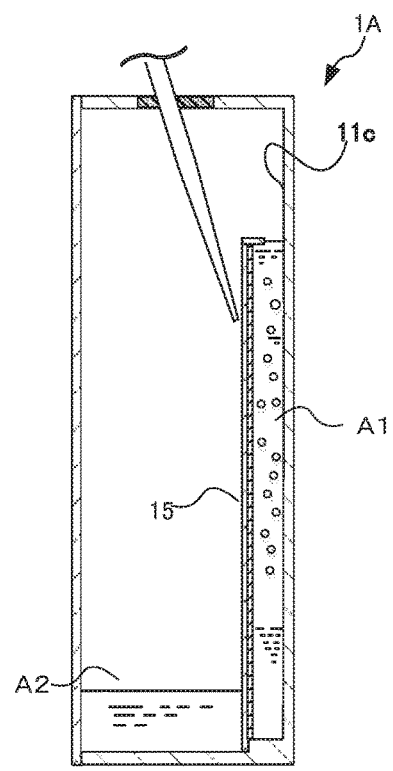
Figure 3C:
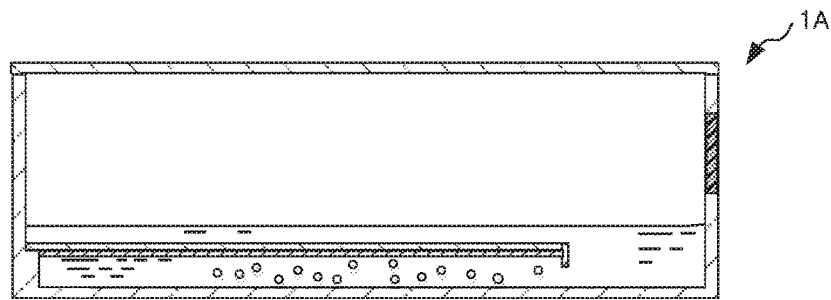
Figure 3D:
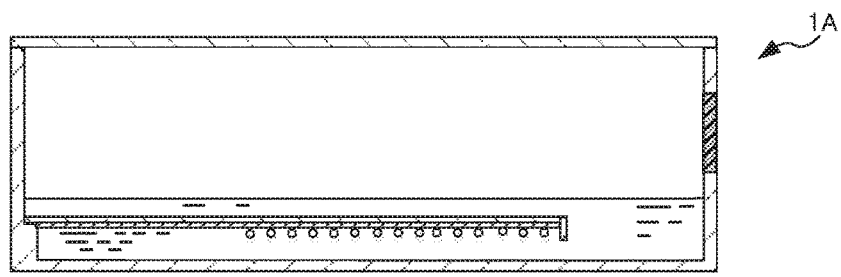
Figure 3E:
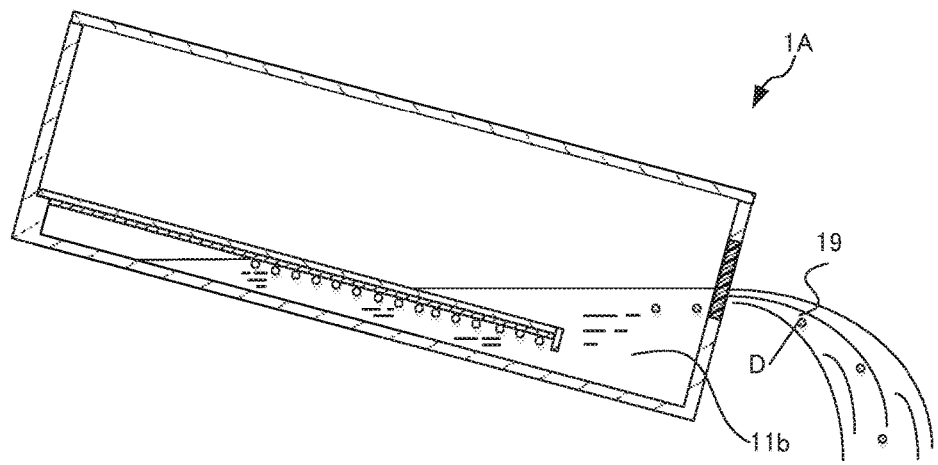

Additionally, by virtue of the presence of the partition plate 15, the mature adipocytes C cannot readily flow out of the culture container 1 even when the culture container 1 is tilted as illustrated in FIG. 3E. Thus, removal of mature adipocytes D having failed to undergo differentiation, along with replacement of the medium, can easily be accomplished by slightly tilting the culture container 1 while the mature adipocytes C are prevented from flowing out of the container. Thus, the step of inverting the culture container is not required, unlike in the conventional method. Furthermore, since the closed culture region A1 is formed by the partition plate 15 and culture container body 11, the flow of the medium is controlled so that a mild environment is created. This promotes differentiation of the mature adipocytes C.

It is preferable for the partition plate 15 to include an edge plate 15*a* along the end (edge) thereof adjacent to the opening 11*b*, the edge plate 15*a* projecting toward the bottom 11*c*. The reason is that, in this case, the mature adipocytes C can be prevented from flowing out of the culture region A1 to the non-culture region A2 during culture of the mature adipocytes C. Additionally, the mature adipocytes C can be prevented from flowing out of the container during replacement of the medium (sample fluid).

Figure 3F:
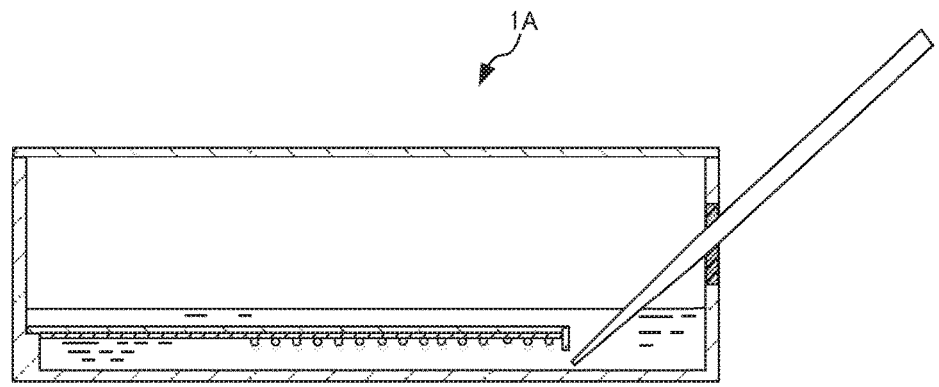

The culture container 1 is preferably configured so that the culture region A1 and non-culture region A2 inside the culture container body 11 are connected via the opening 11*b* defined by the one end of the partition plate 15 and the culture container body 11. For example, as illustrated in FIG. 1B, a supporting portion 11*a* that is approximately U-shaped in the top view may be provided to support the partition plate 15, and the partition plate 15 may be placed on the supporting portion 11*a* in such a manner that the edges of the partition plate 15 other than the edge adjacent to the opening 11*b* are in contact with the side surfaces of the container body 11. With this configuration, mature adipocytes can, as illustrated in FIG. 3A, be seeded with a Pasteur pipette via the opening 11*b*, and DFAT cells can, as illustrated in FIG. 3F, be easily collected with a Pasteur pipette via the opening 11*b* after the cells are dissociated by trypsin.

The culture container 1 includes the sample inlet/outlet 19 provided either in the culture container body 11 or in the ceiling 13. The location of the sample inlet/outlet 19 is not particularly limited as long as samples can be withdrawn or sucked through the sample inlet/outlet 19. In order to facilitate introduction and withdrawal of samples, it is preferable, as illustrated in FIG. 1A, to provide the sample inlet/outlet 19 in the side surface of the container body 11 that is adjacent to the opening 11*b*.

The material of the culture container is not particularly limited, and any transparent material that permits easy observation of the interior of the container and that causes no contamination of samples can be used. Examples of the transparent material include plastic materials such as acrylic resins and glass materials. It is preferable that the culture surface on which cells are cultured be subjected to hydrophilization treatment such as corona discharge treatment or plasma discharge treatment.

The culture container body 11 and ceiling 13 may be configured to be detachable from each other or may be formed integrally with each other. From the viewpoint of ease of washing of the culture container 1 and ease of discharge of mature adipocytes, the ceiling 13 is preferably configured to be detachable from the culture container body 11. The reason is that detaching the ceiling 13 and the temporarily fixed partition plate 15 after completion of culture makes it possible to withdraw DFAT cells to the outside of the container while allowing the DFAT cells to remain adhered to the partition plate and makes it easy to wash the culture region A1.

The partition plate 15 and culture container body 11 may be permanently secured to each other, for example, by means of an adhesive or may be detachably assembled. To assemble the partition plate 15 and culture container body 11 detachably, for example, the partition plate and container body may be joined by fitting, may be joined by using a magnetic force of a magnet embedded in the supporting portion 11*a* or partition plate 15, or may be joined by using an adhesive for temporal fixing.

The distance d between the partition plate and bottom in FIG. 1A is preferably 3.5 mm to 5 mm. If the distance is smaller than the lower limit, it is difficult to perform ceiling culture, while if the distance is greater than the upper limit, the medium (sample fluid) has difficulty spreading over the culture region because of surface tension.

The applications of the culture container 1 are not particularly limited. In light of the above advantageous effects, the culture container 1 is preferably used as a container for ceiling culture for dedifferentiation of mature adipocytes. With the culture container 1 and a culture method using this container, a large amount of adipocytes can be cultured at one time with easy handling.

(Culture Container According to Second Embodiment)

Figure 2A:
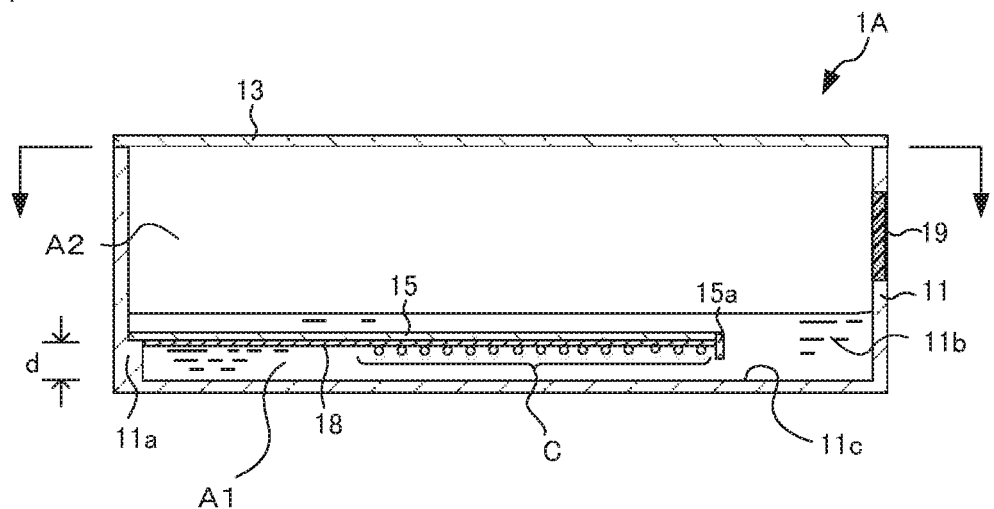
FIG. 2A is a side cross-sectional view illustrating a culture container according to the second embodiment which is in use.
Figure 2B:
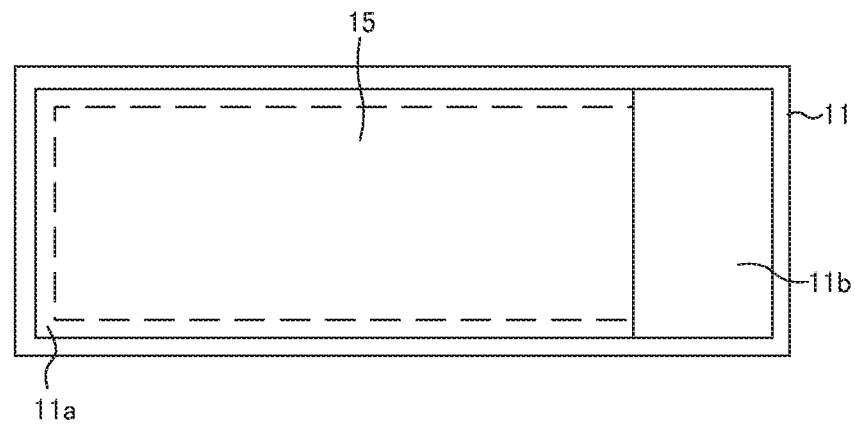
FIG. 2B is a top view illustrating the culture container without the ceiling.

FIG. 2A is a side cross-sectional view illustrating a culture container 1A according to the second embodiment which is in use. FIG. 2B is a top view illustrating the culture container according to the second embodiment without the ceiling. The difference from the culture container according to the first embodiment will be mainly described.

As illustrated in FIG. 2A, the culture container 1A includes the components of the culture container according to the first embodiment, and the partition plate 15 further includes an adhesive layer 18 on the bottom 11*c*-facing major surface.

According to the second embodiment, the provision of the adhesive layer 18 in the partition plate 15 can increase the efficiency of adhesion and culture of the mature adipocytes C. The reason for this has not been clarified. However, it can be inferred that the adhesive layer 18 serves as a scaffold for the mature adipocytes C (or DFAT cells) and thereby allows culture of the mature adipocytes C to proceed efficiently.

The adhesive layer 18 is not particularly limited as long as it can promote dedifferentiation of the mature adipocytes C. Examples of the adhesive layer 18 include laminin, fibronectin, type I collagen, and gelatin. Among these, laminin and fibronectin are preferred. These may be used alone, or two or more thereof may be used in combination.

The applications of the culture container 1A are not particularly limited. In light of the above advantageous effects, the culture container 1A is preferably used as a container for ceiling culture for dedifferentiation of mature adipocytes.

(Method of Dedifferentiating Mature Adipocytes)

A method of dedifferentiating adipocytes using the culture container of FIG. 2A will be described.

(a) First, the culture container 1A of FIG. 2A is prepared. In this example, a culture container 1A having a volume of 75 to 150 cm$^2$ and including an adhesive layer 18 formed of fibronectin is prepared.

(b) A cell suspension containing mature adipocyte is prepared. Specifically, adipocytes are subjected to enzyme treatment with collagenase, and the enzyme-treated cells are subjected to chopping and then to shaking at 37° C. for about 35 minutes. This is followed by filtration. Next, the fluid containing mature adipocyte is centrifuged, and the supernatant is collected. The mature adipocytes become suspended due to containing a larger amount of fat than other cell groups. The suspended mature adipocytes are isolated. The isolated mature adipocytes are added to a medium. For example, the mature adipocytes (about 100 µl, 0.5 to 2×10$^6$ cells) are added to 38 ml of a medium (20% fetal bovine serum-supplemented DMEM). In this way, a cell suspension containing mature adipocyte (0.5 to 2×10$^6$ cells) is obtained.

(c) Next, as illustrated in FIG. 3A, the culture container 1A is positioned upright in such a manner that the partition plate 15 extends perpendicular to the bench (not illustrated). The culture region A1 bounded by the partition plate 15 and bottom 11c is then filled with the cell suspension. Subsequently, as illustrated in FIG. 3B, about 10 ml of a medium was added to the non-culture region A2 bounded by the partition plate 15 and ceiling 13. After that, as illustrated in FIG. 3C, the culture container 1A is returned to a position for normal culture, so that the partition plate 15 inside the culture container 1A is immersed in the medium. It should be confirmed that the mature adipocytes spread uniformly over the culture region A1 of the culture container 1.

(d) Next, the culture container 1A is allowed to stand in a CO$_2$ incubator to continue the culture of the mature adipocytes. As illustrated in FIG. 3D, the mature adipocytes suspended in the medium begin to adhere to the partition plate 15 via the adhesive layer 18. The mature adipocytes come to produce DFAT cells presenting a fibroblast-like form through cell division after two or three days from the start of the culture (the introduction of the cells into the culture container). The DFAT cells thus produced repeat cell division and proliferation, with the result that a colony is formed after about one week from the start of the culture.

(e) When the formation of a colony has been observed, mature adipocytes having failed to dedifferentiate are discharged, along with which the medium is replaced. For example, as illustrated in FIG. 3E, the culture container 1A is slightly tilted relative to the bench (not illustrated), and a portion of the medium and the mature adipocytes D having failed to dedifferentiate are discharged from the culture region A1 to the outside of the culture container 1A through the opening 11b and sample inlet/outlet 19. Due to the presence of the partition plate 15, the mature adipocytes C cannot readily flow out of the culture container 1 even when the container is tilted. Thus, removal of the mature adipocytes D having failed to adhere to the partition plate can easily be accomplished along with replacement of the medium while the flowing out of the mature adipocytes C is prevented. Additionally, the presence of the edge plate 15a ensures effective prevention of the flowing out of the mature adipocytes C. The angle of the tilting is not particularly limited as long as the mature adipocytes D having failed to dedifferentiate are discharged to the outside of the culture container 1A through the sample inlet/outlet 19. The angle of the tilting is preferably 90 degrees or less relative to the surface on which the culture container 1A is placed. A fresh medium is supplied into the culture region A1 through the sample inlet/outlet 19 and opening 11b.

(f) After the addition of the fresh medium, normal adhesion culture is carried out. The DFAT cells continue to actively proliferate, and reach confluence after about two weeks from the start of the culture. Then, the DFAT cells are dissociated by trypsin, and subsequently collected with, for example, a Pasteur pipette as illustrated in FIG. 3F.

Figure 3G:
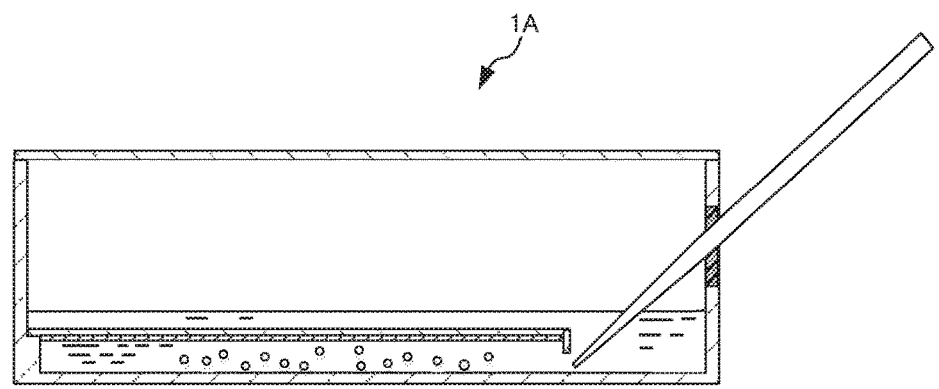

In the step illustrated in FIG. 3A, the culture container 1A is positioned upright in such a manner that the partition plate 15 extends perpendicular to the bench. However, the present invention is not limited by this step. For example, as illustrated in FIG. 3G, the bottom of the culture container 1A may be placed horizontally on the bench (not illustrated), and then a step similar to that illustrated in FIG. 3B may be performed. From the viewpoint of keeping the medium and culture atmosphere stable, the step illustrated in FIG. 3G is preferred.

Figure 11:
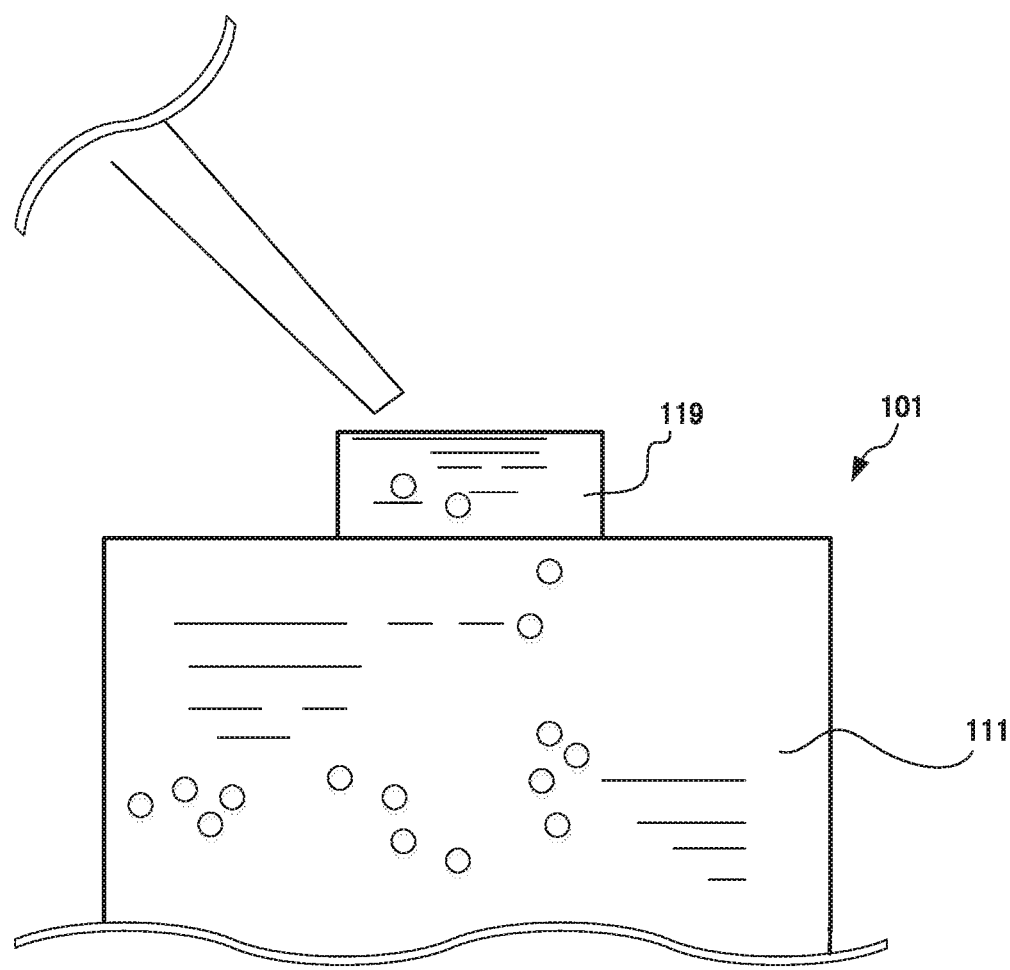
FIG. 11 is a partially enlarged view illustrating how a culture fluid and adipocytes are added to a culture container in a step of the conventional ceiling culture method.

In the conventional ceiling culture, as illustrated in FIG. 11, a medium needs to be added up to the upper edge of the opening of the sample inlet/outlet 119 of the culture container 101. If, therefore, any contaminant adheres to the culture container body 111 or sample inlet/outlet 119, the medium in the culture container 101 can be contaminated due to the contaminant. In contrast, according to the present embodiment in which, as illustrated in FIG. 3A, a medium and mature adipocytes are supplied to the culture region A1 not directly from the sample inlet/outlet 19 but via the air phase in the non-culture region A2, the medium and mature adipocytes C supplied into the culture region A1 do not contact the sample inlet/outlet 19 and are therefore unlikely to be contaminated. Additionally, the medium added in the step illustrated in FIG. 3B encloses the culture region A1 as illustrated in FIG. 3C, and the medium in the non-culture region A2 functions as an intermediate ceiling, which further reduces the likelihood of contamination of the medium and mature adipocytes in the culture region A1.

Figure 10:
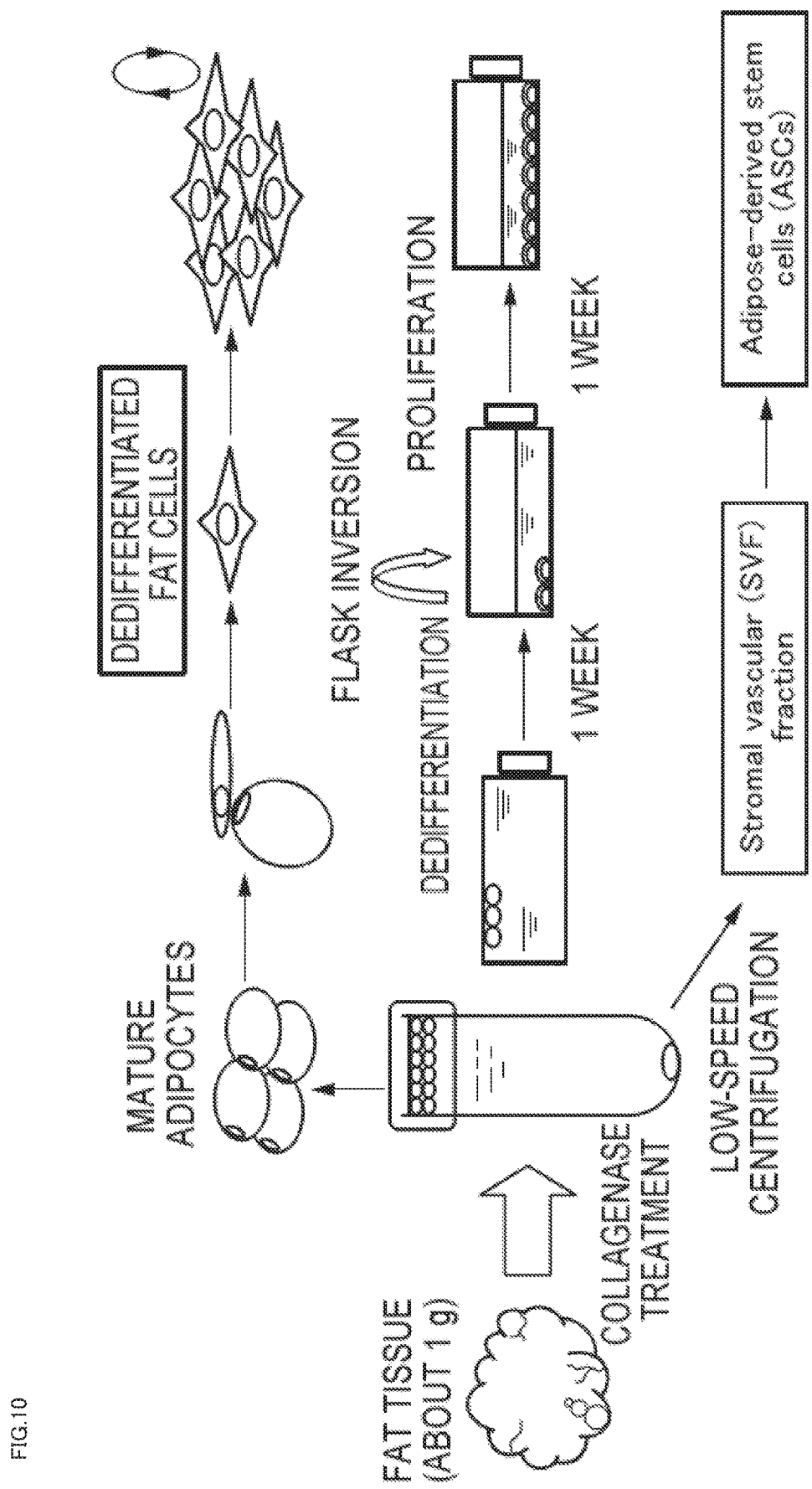
FIG. 10 illustrates the steps of a conventional ceiling culture method.

Considering the future mass production of DFAT cells in view of culture environments and work spaces, it is desirable that a plurality of culture containers can be stacked on top of each other. However, in the conventional ceiling culture method illustrated in FIG. 10, the culture container needs to be inverted by 180 degrees. Thus, if the bench on which culture containers are placed is contaminated (or if any of the culture containers is contaminated), contamination of any of the culture containers can be transmitted to the other culture containers through repetition of the inversion and stacking operation in which a first culture container is inverted and then a second culture container is stacked on the contaminated surface of the first culture container. In contrast, according to the present embodiment, inversion of the culture container 1A is unnecessary, and removal of the mature adipocytes D having failed to dedifferentiate can easily be accomplished along with replacement of the medium merely by, as illustrated in FIG. 3E, slightly tilting the culture container 1A relative to the bench and discharging or sucking the medium. That is, according to the present embodiment, the surface of the culture container that contacts the bench or another culture container on top of which the culture container is placed is always the same and, therefore, even when a plurality of culture containers is stacked on top of each other, a contaminant adhering to any of the culture containers cannot be transmitted to the other culture containers.

A commercially-available culture container such as a multiple culture container (available from Corning Incorporated under the trade name "FALCON MULTI-FLASK") is merely made up of a plurality of culture container segments stacked on top of each other and lacks a component corresponding to the partition plate in the present invention. If, therefore, the commercially-available multiple culture container is used to carry out ceiling culture of mature adipocytes, a step such as the inversion of the culture container is required as in the conventional ceiling culture, and hence the above-described problem of transmission of contamination arises. Additionally, in order to supply a medium to each culture container segment of the multiple culture container, it is necessary to repeat the cumbersome operation of placing the culture container vertically upright, then tilting the culture container by 45 degrees, and then placing the container horizontally. In contrast, according to the present embodiment, the provision of the partition plate eliminates the need for inversion of the culture container, thereby solving the problem of transmission of contamination. Furthermore, as illustrated in FIGS. 3A through 3C, the culture container can easily be charged with a medium and mature adipocytes without repeated inversion of the container.

OTHER EMBODIMENTS

Although the present invention has been described above with reference to exemplary embodiments, the discussion and figures constituting a part of the present disclosure should not be understood as limiting the present invention. Various alternative embodiments, examples, and applications will be apparent to those skilled in the art from the present disclosure.

For example, the following modifications can be made to the culture containers 1 and 1A according to the first and second embodiments which are respectively illustrated in FIGS. 1A and 2A.

Figure 5:
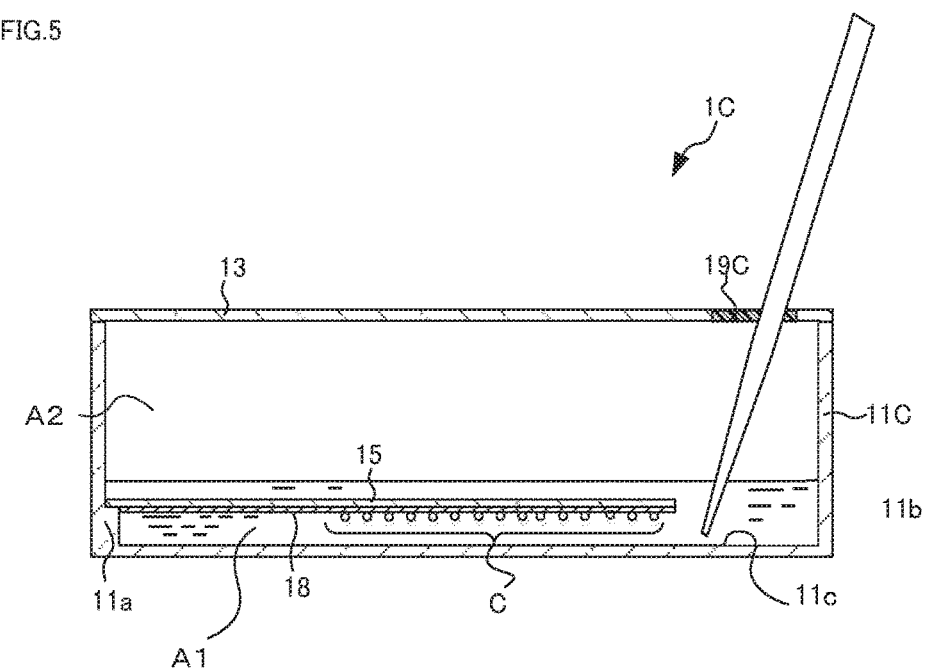
FIG. 5 is a side cross-sectional view illustrating a culture container according to a modified example of an embodiment which is in use.

As illustrated in FIG. 5, the sample inlet/outlet 19 may be provided in the upper surface of the ceiling 13. In this case, the sample inlet/outlet 19C is preferably implemented by a septum cap or embedded cap so that the upper surface of the ceiling 13 and the sample inlet/outlet 19C are flush with each other. The reason is that, in this case, the culture containers can easily be stacked on top of each other and can easily be placed on a microscope stage. To simplify the culture container, the edge plate may be omitted from the partition plate 15. However, it is preferable to provide the edge plate to effectively prevent the flowing out of mature adipocytes (or DFAT cells).

Figure 6:
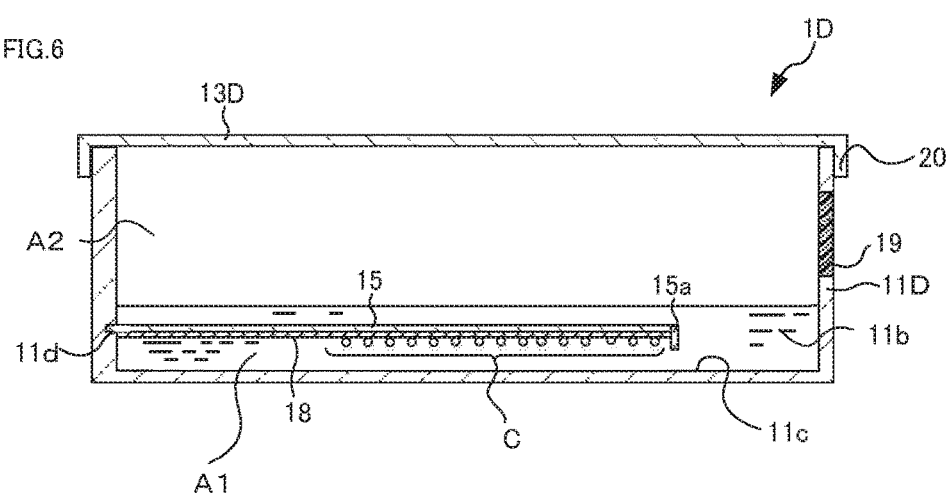
FIG. 6 is a side cross-sectional view illustrating a culture container according to a modified example of an embodiment which is in use.

As illustrated in FIG. 6, a flange 20 may be provided on the periphery of the ceiling 13. The reason is that, in this case, the airtightness of the culture container closed by the ceiling 13 detachably attached to the culture container body is improved, and the reliability of the culture container is improved. The partition plate 15 may be attached by being fitted into a fitting portion 11d of the culture container body.

Figure 7:
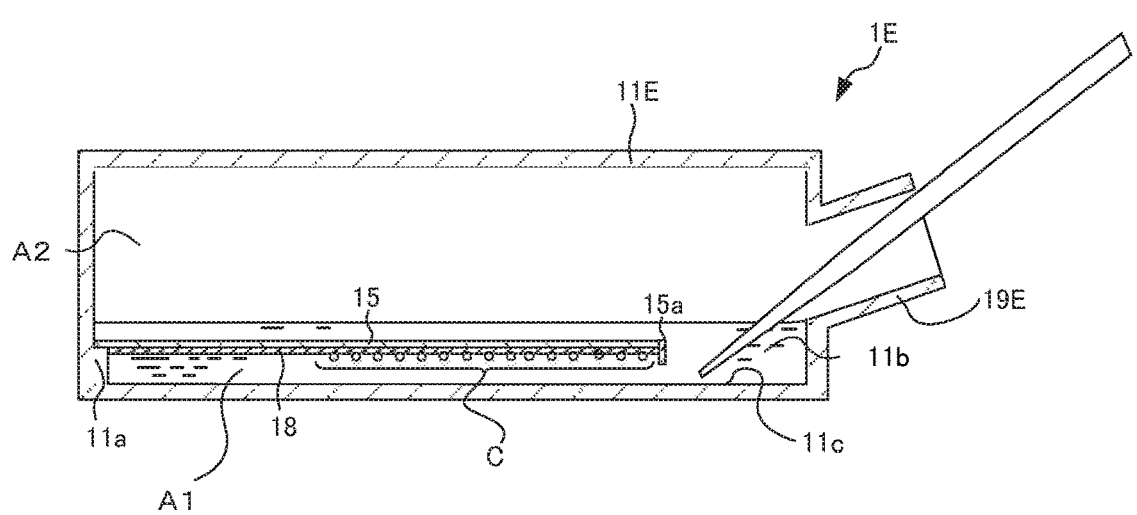
FIG. 7 is a side cross-sectional view illustrating a culture container according to a modified example of an embodiment which is in use.

As illustrated in FIG. 7, the sample inlet/outlet 19 may be embodied as a sample inlet/outlet 19E provided in a side surface of a culture container body 11E and being in the form of a long neck slightly inclined upwardly relative to the bottom 11c. The reason is that, in this case, the medium can easily be discharged to the outside of the culture container at the time of replacement of the medium. To facilitate the discharge of the medium, a slope extending from the base of the sample inlet/outlet 19E to the bottom 11c may be provided, although such a slope is not illustrated in the figure. It is preferable to adjust the length and angle of the slope and therefore the distance from the edge plate 15a to the sample inlet/outlet 19E so as to allow the pipette to reach the edge plate 15a through the opening of the sample inlet/outlet 19E. In the culture container, the ceiling may be formed integrally with the culture container body rather than being detachable from the culture container body.

Figure 8A:
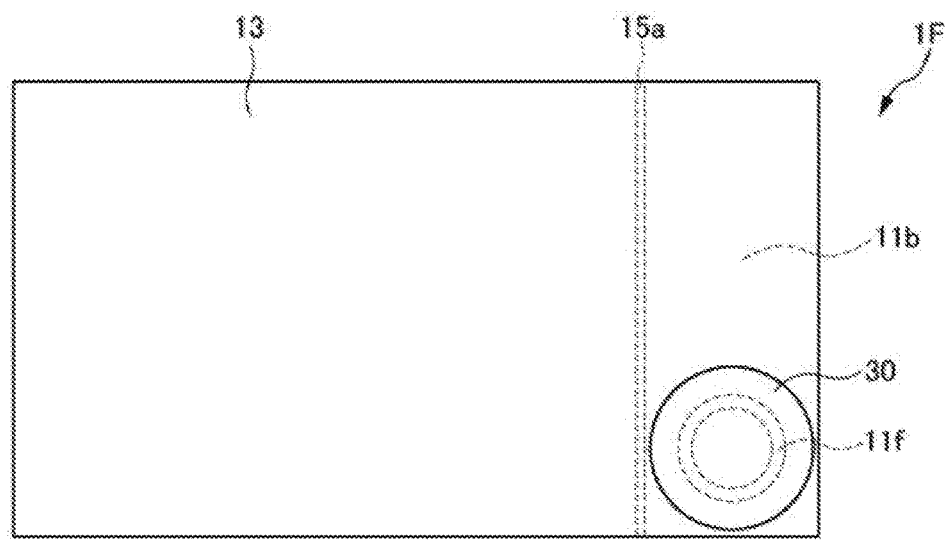
FIG. 8A is a top view of a culture container according to a modified example of an embodiment.
Figure 8B:
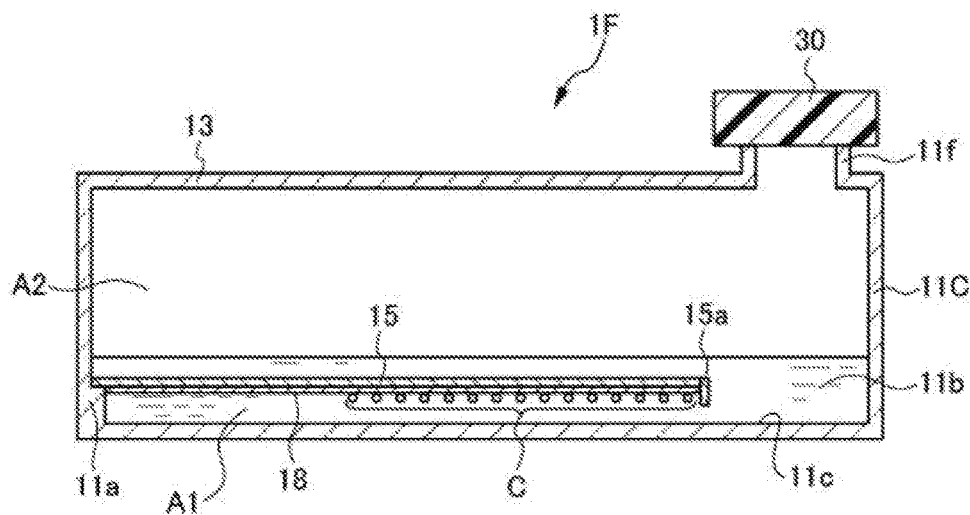
FIG. 8B is a cross-sectional view illustrating the culture container in use.
Figure 8C:
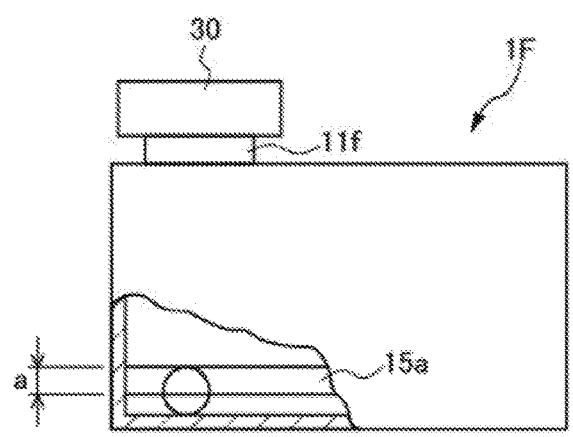
FIG. 8C is a side view of the culture container.

FIGS. 8A through 8C illustrate a culture container 1F which is a modified example of the culture container 1C of FIG. 5. A sample inlet/outlet 11f may, as illustrated in FIG. 8A, be located at the lower right position in the top view of the culture container 1F, and the opening 1ib may, as illustrated in FIG. 8B, be provided below the sample inlet/outlet 11f. The reason is that, in this case, the provision of the sample inlet/outlet 11f in the ceiling makes it easy to introduce and withdraw samples using a pipette. Additionally, the DFAT cells can easily be collected from the culture container 1F by tilting the culture container 1F to cause the DFAT cells to gather at that site located below the sample inlet/outlet 11f which is indicated by a circle in FIG. 8C.

It is preferable that, as illustrated in FIG. 8B, the sample inlet/outlet 11f be formed to project from the surface of the ceiling 13 and be closable with a screw cap 30. The reason is that, in this case, the cap 30 can easily be attached and detached when the culture container is used in an isolator.

For convenience of illustration, the sample inlet/outlet 11f is assumed to be located at the lower right position in the top view. However, the location of the sample inlet/outlet 11f is not particularly limited, and the sample inlet/outlet 11f may be located at any position within the rectangle representing the ceiling 13.

Figure 9A:
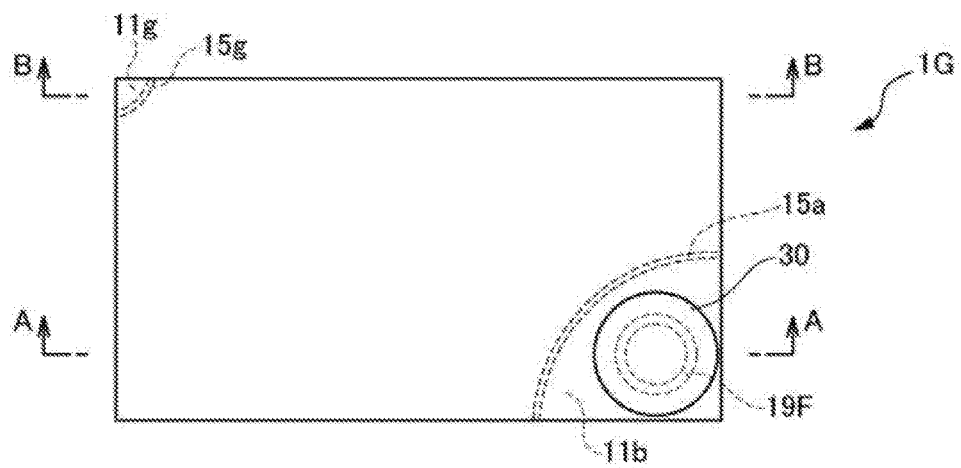
FIG. 9A is a top view of a culture container according to a modified example of an embodiment.
Figure 9B:
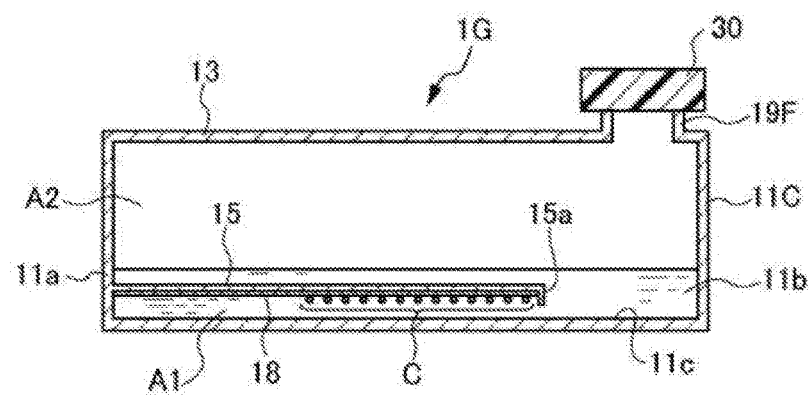
FIG. 9B is a side cross-sectional view (along the line A-A) illustrating the culture container in use.

FIGS. 9A through 9D illustrate a culture container 1G which is a modified example of the culture container 1F of FIG. 8A. One end (15a) of the partition plate 15 may, as illustrated in FIG. 9A, be in the shape of a parabola surrounding the sample inlet/outlet 19F as indicated by a dashed line in the top view of the culture container 1G, and the opening 1ib defined by the one end of the partition plate 15 and the culture container body 11C may be formed. The reason is that the formation of the opening 1ib of such a shape increases the surface area of the partition plate 15 and therefore broadens the region for culture of DFAT cells.

Figure 9C:
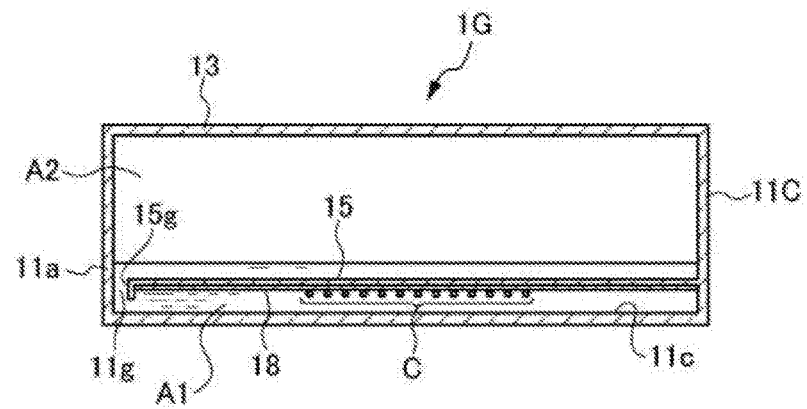
FIG. 9C is a side cross-sectional view (along the line B-B) illustrating the culture container in use.
Figure 9D:
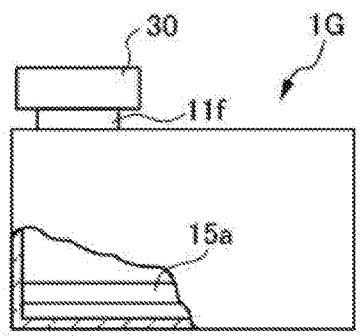
FIG. 9D is a side view of the culture container.

As illustrated in FIG. 9A and FIG. 9C, an air hole 11g may be formed on the diagonal of the partition plate 15 so as to be opposed to the opening 11b. The reason is that, in this case, the medium can readily flow during collection of DFAT cells and thus the DFAT cells can easily be collected.

The air hole 11g may, like the opening 11b, be defined by the culture container body 11C and an end of the partition plate 15, or may alternatively be a communication hole that is provided in the partition plate 15 at a position adjacent to an end of the partition plate 15 and that extends from the ceiling-facing major surface of the partition plate 15 to the bottom-facing major surface of the partition plate 15. It is sufficient for the air hole 11g to perform the function as an air hole. Thus, from the viewpoint of maximizing the surface area of the partition plate 15, the diameter of the air hole 11g is preferably smaller than the diameter of the opening 11b.

In order to prevent the mature adipocytes C from flowing out of the culture region A1 to the non-culture region A2 during culture of the mature adipocytes C, it is preferable to equip the partition plate with edge plates 15a and 15g extending along the edge of the opening 11b and along the edge of the air hole 11g, respectively.

From the foregoing, it should be appreciated that the present invention encompasses various other embodiments which are not described herein. The technical scope of the present invention may therefore be limited only by the inventive features set forth in the claims deemed reasonable from the above description.

EXAMPLES

Reference Example 1

To investigate the effect of the adhesive layer on the adhesion and culture of adipocytes, mature adipocytes were isolated according to step (b) in the above method for dedifferentiating mature adipocytes, and then the adipocytes were seeded. The method and conditions for the experiment are described below.

(Isolation of Mature Adipocytes)

Human subcutaneous fat was obtained from the buttocks of an 85-year-old woman by agreement in accordance with the regulations of the Ethics Committee of Nihon University. The obtained mature adipocytes were washed and then treated with collagenase. The treated cells are subjected to chopping and then to shaking at 37° C. for about 35 minutes. This was followed by filtration. Next, the fluid containing the mature adipocytes was centrifuged (at 700 rpm for 1 minute), and the supernatant was collected and washed. The process of centrifugation and washing was repeated again. An Eppendorf tube was charged with 1 ml of DMEM+2% FBS, in which the isolated mature adipocytes were suspended. In this manner, a cell suspension containing mature adipocytes (mature adipocyte suspension) was obtained.

(Seeding of Mature Adipocytes)

(a) Sterilized silicon O-rings (P-11.2 (JASO-2011 [SI50], O-Ring Sogo Kenkyusho) were placed on the bottoms of the wells of a 24-well plate using curved tweezers.

(b) Next, the mature adipocyte suspension was prepared in such a manner that 2.5 µl of a adipocyte layer would be formed relative to 350 µl of DMEM+10% FBS in each well. 350 µl of the suspension was added to each well within the inner diameter of the O-ring (this means that about 1400 mature adipocytes were introduced per well). Samples were prepared in a total of 24 wells for six types of coated coverslips; specifically, six groups each consisting of four wells were created and were each allocated to a different type of coverslip.

(c) The coverslip was placed on the O-ring, and another O-ring was placed on the coverslip to prevent lifting of the coverslip. The medium leaking from the periphery of the coverslip was sucked and removed.

(d) 1 ml of DMEM+10% FBS was added, and the well plate was shaken all around under a microscope to cause the mature adipocytes to be distributed uniformly over the ceiling.

(e) This was followed by incubation in a 5% $CO_2$ atmosphere at 37° C. for 15 days.

(Types of Coverslips)

The following six types of coverslips were prepared as simulated partition plates. The combinations of the base material and adhesive layer (coating) are listed below.

Partition plate 1: Plastic/No coating (cell disk, 13.3 mm round, 0.1 mm thick, LF1 (MS-92132), Sumitomo Bakelite Co., Ltd.)

Partition plate 2: Glass/No coating (micro cover glass No. 1, 15 mm round, 0.12 to 0.17 mm thick, Matsunami Glass Ind., Ltd.)

Partition plate 3: Glass/Collagen (NEU GG-14-collagen, 14 mm round, No. 1 thickness, Cosmo Bio Co., Ltd.)

Partition plate 4: Glass/Gelatin (NEU GG-14-gelatin, 14 mm round, No. 1 thickness, Cosmo Bio Co., Ltd.) Partition plate 5: Glass/Laminin (NEU GG-14-laminin, 14 mm round, No. 1 thickness, Cosmo Bio Co., Ltd.) Partition plate 6: Glass/Fibronectin (NEU GG-14-fibronectin, 14 mm round, No. 1 thickness, Cosmo Bio Co., Ltd.)

(Evaluation Method)

Fixation with 4% paraformaldehyde was performed and followed by nuclear stain with DAPI. A fluorescence microscope, BZ-X710, (Keyence Corporation), was used to create a phase contrast image of the entire coverslip and a composite image of the DAPI-stained images. Spindle-shaped cells having no lipid droplets were determined to be DFAT cells. The total number of the DFAT cells was calculated for each group as the sum of the numbers of the DFAT cells in the four wells, and the total numbers of the DFAT cells were compared among the six groups. The number of the seeded adipocytes was 5600 (1400×4 wells). According to the graph of FIG. 4, the total number of DFAT cells were produced from the 5600 adipocytes.

Figure 4:
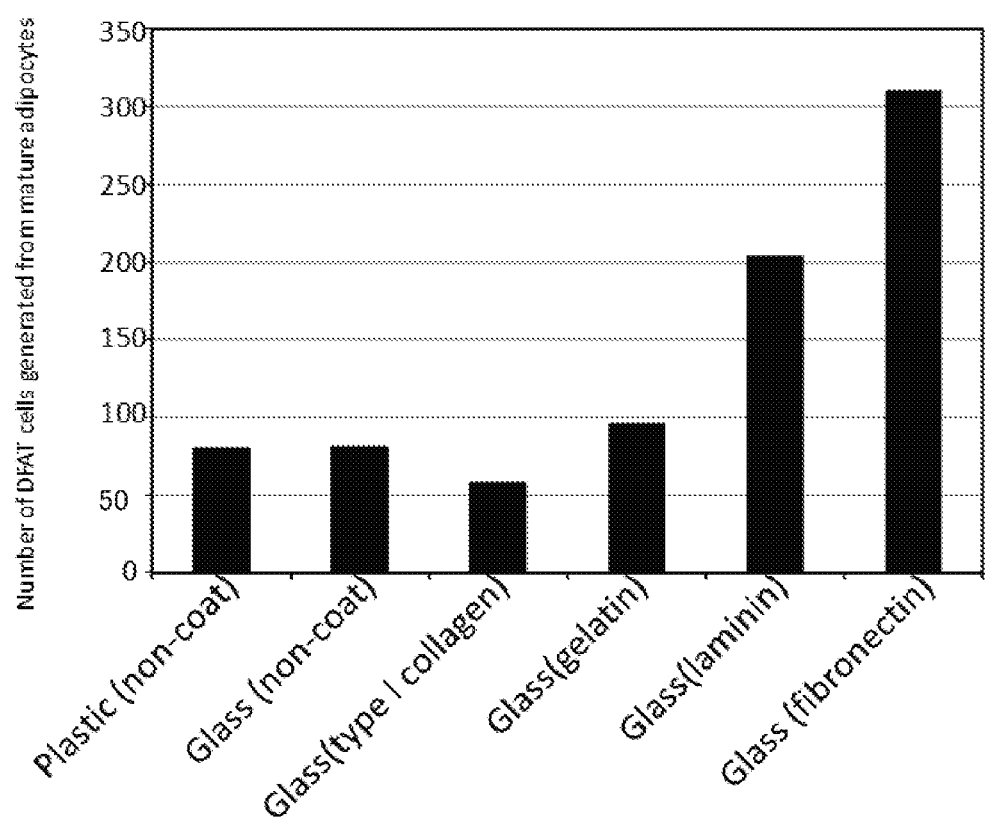
FIG. 4 is the results of a test for the effect of adhesive layers on the number of DFAT cells.

The obtained results are collectively illustrated in FIG. 4. It was thus demonstrated that laminin and fibronectin can promote dedifferentiation of mature adipocytes.

INDUSTRIAL APPLICABILITY

The present invention is useful particularly for preparing DFAT cells which have been under development as therapeutic cells, and is applicable to ceiling culture of adipocytes on a wide range of scales ranging from laboratory-scale ceiling culture to commercial-scale ceiling culture complying with Good Manufacturing Practice (GMP) concerning pharmaceutical products etc. The advancement of commercial production of DFAT cells will promote research aimed at establishment of cell therapy for disorders that frequently occur in elderly people, for which no particular effective therapy has existed, and that seriously impair the quality of life (QOL) of the affected patients, such as, in particular, intractable peripheral arterial disease (PAD) and bone fracture associated with osteoporosis. Furthermore, various applications for addressing many disorders are expected, such as regeneration of cartilage against osteoarthritis, regeneration of vesicourethral smooth muscle in atrophic bladder, resolution of graft failure after hematopoietic stem cell transplantation, and prevention of graft-versus-host disease (GVHD).

REFERENCE SIGNS LIST 1, 1A through 1G Culture container
11, 11A through 11E Culture container body
11a Supporting portion
11b Opening
11c Bottom
11g Air hole
13 Ceiling
15 Partition plate
15a, 15g Edge plate
18 Adhesive layer
19, 19E, 19F Sample inlet/outlet
A1 Culture region
A2 Non-culture region
C Mature adipocytes

What is claimed is:

1. A culture container comprising:
    a culture container body;
    a partition plate disposed in a vicinity of a bottom of the culture container body to face the bottom so that a culture region is formed between the partition plate and the bottom, the partition plate defines the culture region and a non-culture region in the culture container body, and a distance between the partition plate and the bottom is 3.5 mm to 5 mm; and
    a sample inlet/outlet provided in a side surface or a ceiling above the culture region of the culture container body, being adjacent to an opening of the culture container,
    the culture region and the sample inlet/outlet communicating with each other via the non-culture region and the opening that is formed adjacent to one end of the partition plate,
    wherein the partition plate comprises an edge plate along an edge of the opening, the edge plate projecting toward the bottom.

2. The culture container according to claim 1, wherein the partition plate comprises an adhesive layer on a major surface thereof facing the bottom.

3. The culture container according to claim 2, wherein the adhesive layer is selected from a group consisting of laminin, fibronectin, type I collagen, and gelatin.

4. The culture container according to claim 1, wherein an air hole is defined by the culture container body and another end of the partition plate at a position remote from the opening.

5. The culture container according to claim 4, wherein the opening and the air hole are provided opposed to each other on a diagonal of the partition plate.

6. The culture container according to claim 1, wherein the culture container is a container configured for ceiling culture for dedifferentiation of adipocytes.

7. The culture container according to claim 1, wherein the partition plate has a nonporous material structure.

8. A method of dedifferentiating adipocytes, comprising:
    charging a culture region of a culture container with mature adipocytes and a culture fluid, the culture container comprising: a partition plate disposed in a vicinity of a bottom of the culture container to face the bottom so that the culture region is formed between the partition plate and the bottom, and a distance between the partition plate and the bottom is 3.5 mm to 5 mm, the partition plate defines the culture region and a non-culture region in the culture container; and a sample inlet/outlet provided in a side surface or a ceiling above the culture region of the culture container, being adjacent to an opening of the culture container, and the sample inlet/outlet communicating with the culture region via the non-culture region and the opening of the culture container; wherein the partition plate comprises an edge plate along an edge of the opening, the edge plate projecting toward the bottom,
    adhering the mature adipocytes suspended in the culture fluid to the partition plate; and
    slightly tilting the culture container to discharge a portion of the culture fluid and mature adipocytes having failed to dedifferentiate from the culture region to an outside of the culture container through the opening and the sample inlet/outlet.

9. The method of dedifferentiating adipocytes according to claim 8, wherein, in the adhering, the mature adipocytes are adhered to the partition plate via an adhesive layer.

10. The method of dedifferentiating adipocytes according to claim 8, wherein an angle of the tilting is 90 degrees or less.

11. The method of dedifferentiating adipocytes according to claim 8, wherein the opening provides access to permit the charging of the culture region via the non-culture region inside the culture container, and the opening is disposed to overlap with the partition plate in a plane within which the partition plate is disposed.

12. A culture container comprising:
    a culture container body;
    a partition plate disposed in a vicinity of a bottom of the culture container body to face the bottom so that a culture region is formed between the partition plate and the bottom, the partition plate defines the culture region and a non-culture region in the culture container body, and a distance between the partition plate and the bottom is 3.5 mm to 5 mm; and
    a sample inlet/outlet provided in a side surface or a ceiling above the culture region of the culture container body, being adjacent to an opening of the culture container,
    the culture region and the sample inlet/outlet communicating with each other via the non-culture region and the opening that is formed adjacent to one end of the partition plate, the opening providing access to permit a filling of the culture region via the non-culture region inside the culture container body, and the opening being disposed to overlap with the partition plate in a plane within which the partition plate is disposed,
    wherein the partition plate comprises an edge plate along an edge of the opening, the edge plate projecting toward the bottom.

* * * * *